(12) United States Patent
Steg

(10) Patent No.: US 6,488,663 B1
(45) Date of Patent: Dec. 3, 2002

(54) INFUSION APPARATUS FOR ADMINISTERING A MEDICINE

(75) Inventor: Henning Steg, Tyresö (SE)

(73) Assignee: Arta Plast AB, Tyresö (SE)

( * ) Notice: Subject to any disclaimer, the term of this patent is extended or adjusted under 35 U.S.C. 154(b) by 0 days.

(21) Appl. No.: 09/875,273

(22) Filed: Jun. 7, 2001

(30) Foreign Application Priority Data

May 9, 2001 (EP) ............................................. 01111331

(51) Int. Cl.[7] .................. A61M 11/00; A61M 5/178; A61M 5/00
(52) U.S. Cl. ............... 604/164.08; 604/93; 604/165.01; 604/283; 606/167; 606/170
(58) Field of Search ................. 604/164.01, 164.02, 604/164.03, 164.08, 164.09, 164.11, 165.01, 165.02, 165.04, 167.01, 167.02, 167.06, 170.01, 170.02, 264, 22, 104, 158; 606/167, 170

(56) References Cited

U.S. PATENT DOCUMENTS

| | | | | |
|---|---|---|---|---|
| 5,423,775 A | * | 6/1995 | Cannon | 604/283 |
| 5,522,803 A | * | 6/1996 | Teissen-Simony | 604/177 |
| 5,632,735 A | * | 5/1997 | Wyatt et al. | 604/283 |
| 5,728,071 A | * | 3/1998 | Watson et al. | 604/180 |
| 6,056,718 A | * | 5/2000 | Funderbunk et al. | 604/93 |

* cited by examiner

*Primary Examiner*—David J. Walczak
*Assistant Examiner*—Anuradha Ramana
(74) *Attorney, Agent, or Firm*—Klaus J. Bach (57) ABSTRACT

In an infusion apparatus for supplying a medicine into the body of a patient which infusion apparatus comprises a first element including a cannula and a second element including an injection needle which is placed in sealing communication with the cannula when the first and second elements are joined, the second element includes a circular groove and the first element includes locking members which are slidably movable back and forth into, and out of, the groove for selectively engaging said second element to lock it when inserted into the first element.

20 Claims, 6 Drawing Sheets

Fig. 2

Section A - B

INFUSION APPARATUS FOR ADMINISTERING A MEDICINE

BACKGROUND OF THE INVENTION

The invention resides in an infusion apparatus for administering a medicine to the body of a human or an animal, comprising at least a first element provided with a cannula for insertion into, and installation in, the body, and a second element including a hollow injection needle which is connected to a hose for the supply of the medicine, wherein the first and the second element can be releasably joined by way of a locking element so that the medicine can be supplied from the hose through the needle into the cannula.

Such injection equipment is known for example from EP-B 0 688 232. Many attempts—including the arrangement disclosed in the reference—have been made which aimed at facilitating the handling of such equipment not only for the medical personnel such as the physicians, the nurses and other caregivers but also for the patient that is the person who handles such infusion equipment during self-treatment. Persons suffering from diabetes for example have to administer their medicines regularly by themselves either by injection of the medication by conventional injection syringes or by way of injection apparatus of the type with which the present invention is concerned.

It is pointed out that, with the type of infusion apparatus with which the present invention is concerned, basically any medicine can be introduced into the body of a human or an animal that is, the infusion apparatus is not limited to the administration of insulin.

Infusion apparatus of the type with which the present invention is concerned have been found to be particularly suitable for persons who have to be treated with a particular medicine regularly in certain time intervals since continuous new puncturing of the skin and the veins or arteries can be avoided in this way. In this way, pain and often hematoma-causing punctures of injection needles are limited to a minimum. Furthermore, people who need to use injection apparatus of the type with which the present invention is concerned are generally already quite weak as a result of the condition requiring the administration of the medicine. If then, in addition to such physical weakness, the person develops a mental repugnance and as a result, a certain insecurity, the use of infusion apparatus known in the art may result in inappropriate handling or in faulty operation. For example, in prior art infusion apparatus a connection between the first and second elements can only be established when the two elements are oriented in a predetermined way with respect to each other—depending on the particular design.

Relative angular displacement of the first and second elements for example by 180° that is, relative angular positions other than that for which the apparatus is designed will not permit a jointure of the elements. And even if the angular orientations of the two elements is correct a connection can still not be established if the two elements are slightly displaced laterally since, in addition to the locking elements, there are provided guide elements which are disposed in the same plane and which must be properly oriented so as to fit into the guide openings of the other element in order to permit joining and interlocking of the two elements.

An ill person, particularly at an advanced age, is generally not in a position to orient the two elements properly angularly and, at the same time, laterally. Furthermore, the two elements must generally be interconnected with one hand, since the cannula of the infusion apparatus is inserted for example in the vein of the other arm so that the hand of this arm is not available for the connecting procedure.

It is finally to be note that the prior art infusion apparatus as disclosed in the cited EP patent includes two tongue-like locking elements and two pin-like guide elements, and further, locking element guide structures and two openings for receiving the guide pins which all have to be fitted to one another. Their manufacture requires high precision tools which themselves are complicated and expensive. Furthermore, as a result, also the manufacture of the known infusion apparatus requires highest precision so that proper fit of the guide and locking structures is ensured. This implies of course that also the needle in the second element is properly axially oriented and inserted into the opening of the cannula in the first element when the two elements are interconnected. Consequently, not only the manufacturing tools for making the known infusion apparatus are expensive but also the process of manufacturing the infusion apparatus is expensive and difficult since a continuous precise orientation of all the parts to be engaged with one another is to be ensured.

It is therefore the object of the present invention to provide an infusion apparatus with which an inexperienced user as well is a weak user can insert, in a simple manner, the cannula into the body and can establish the connection with the infusion apparatus for the introduction of the medicine into the body by way of the two interconnected elements. It should not be necessary to accurately orient the two elements to be interconnected in an accurate rotational position with respect to each other and the two element should be easy to be inter-locked and to be disconnected. Furthermore, the needle of an element should be automatically oriented precisely with respect to the insert opening of the other element. Also, the infusion apparatus should be easy and inexpensive to manufacture so that they are affordable and can be used in large numbers.

SUMMARY OF THE INVENTION

In an infusion apparatus or supplying a medicine into the body of a patient which infusion apparatus comprises a first element including a cannula and a second element including an injection needle which is placed in sealing communication with the cannula when the first and second elements are joined, the second element includes a circular groove and the first element includes locking members which are slidably movable back and forth into and out of the groove for selectively engaging the second element to lock it when inserted into the first element.

The apparatus according to the invention has the advantage that the second element can easily be inserted into the first element without the need of maintaining proper rotational relative orientation of the two elements. Actually, the second element only needs to be inserted into a single opening in the first element in a way as it is known from coaxial plugs in the electric or electronic field. No proper rotational orientation must be observed. If the two elements are not axially properly oriented they can clearly not be joined so that a faulty interconnection is not even tried. Unlike the prior art arrangement, the apparatus according to the invention has no guide pins or locking elements, which have to be properly joined for interconnecting the two elements. No locking element needs to be actuated when the two elements are joined and interlocked. For the disconnection the locking element only needs to be disengaged using the thumb and forefinger of one hand. With the simple locking and unlocking mechanism and the precise automatic orientation of the needle relative to the opening of the cannula, the apparatus is still of simple design, whereby also the tooling expenses for the manufacture of such infusion apparatus are drastically reduced so that the apparatus can be manufactured in large number at low costs.

In order to further facilitate the insertion of the second element into the insertion opening formed in the first element, the second element is essentially circular in cross-section and the axis thereof, that is the center-point of the circle, coincides with the needle shaft.

Another feature which facilitates insertion of the second element into the insertion opening in the first element is the provision of an inclined circumferentially extending front end area of the section of the second element to be inserted into the first element. In this way, the insertion of the second element into the insertion opening of the first element is facilitated even when the two elements are not precisely aligned with respect to each other since the second element is automatically moved into proper alignment during the insertion procedure. The inclined circumferential front area of the first element furthermore opens the clamping structure upon insertion of the second element into the insertion opening of the first element. Also, the insertion opening of the first element may be inclined at its open end so that it has a funnel-like shape.

The clamping structure is preferably formed by two separate clamping arms, which are essentially parallel to each other but are resiliently movable away from, and toward, each other. When they are moved toward each other the insertion opening of the first element is unlocked so that the second element can be inserted into the insertion opening of the first element up to a predetermined end position. Upon movement of the clamping arms away from each other the second element is locked to the first element when it is in its predetermined end position.

Preferably, the locking arm include a circle segment area with a radius corresponding to the radius of annular groove formed in the second element by which the locking arms enter the groove for locking the first element to the second element. There are preferably two opposite locking arms and the circle segment spans preferably about a quarter of a circle. With the locking arms engaged in the grooves, the two elements are held firmly engaged with each other.

In order to ensure in a simple manner that the two locking arms forming the locking structure move out of the insert opening of the first element for the insertion of the second element or that they move to an unlocking position when the second element is inserted but is to be released, each locking arm includes an inclined area and the guide slot in the first element is oppositely inclined. For unlocking the two elements from each other the inclined areas of the locking arms slide along the inclined areas of the first element so that the locking arms are elastically moved apart until they are removed from the groove. The return force generated by the elastic deformation of the locking arms is sufficiently large so that the locking arms return to a locking position when the locking structure is released.

In another embodiment of the infusion apparatus, the guide structure for the locking arms extends essentially perpendicularly to the axis of the insertion opening for the second element which insertion opening is essentially circular in cross-section.

The infusion apparatus is equally suitable for use by right-handed and left-handed persons since the two locking arms forming the locking structure are essentially identical in design and are arranged symmetrically to the axis with respect to which they are movable. Also, the cannula is arranged in axial symmetry with this axis. Furthermore, movement of the locking arms for locking and unlocking of the second element occurs by movement along this axis no matter whether the two locking arms are actuated by the fingers of the right or the left hand.

In order to ensure in a simple manner that the path of movement of the locking arms with in the guide slot of the first element is limited the locking arms are preferably provided with engagement projections adapted to reach behind engagement edges, which are formed in the area of the guide structure that is the guide slot of the first element. Consequently, no other measures are needed to retain the locking arms in the guide slots once the locking arms have reached, during assembly, a position in which the engagement projections are disposed behind the engagement edges in the guide slots.

The end of the locking member may be provided with an actuating structure such as an enlarged area, which extends from the body of the first element. The actuating structure facili tates the use of the infusion apparatus for the user. It is advantageous if also the actuating structure is guided in the first element. In this way, the guided support of the whole locking member in the first element is improved.

In order to prevent a slipping of the fingers from the actuating structure the surface as area of the engagement structure, which his grasped by the user, is preferably provided with gripping means such as grooves, furrows or a rough coating.

For the same reason, it is advantageous if the side of the first element opposite the actuating structure is provided at least partially with grip-improving means so that the structure can be safely grasped with a thumb and a finger.

In another advantageous embodiment of the invention, the second element includes at its free end an essentially axial recess into which the needle projects such that its tip does not extend beyond the free end of the second element. In this way, it is ensured that, upon insertion of the second element into the insertion opening of the first element, the user will not contact the needle so that contamination of the needle is avoided and the free end of the needle is not damaged. As a result, a continuous precise axial alignment of the needle with the opening in the cannula in the first element is maintained.

In order to provide for a good mechanical stability between the two elements when they are interconnected, the infusion apparatus is so designed that the opening area of the cannula extends at least partially into the recess of the second element when the two elements are interconnected. In this way, it is ensured that any deformation of the two elements does not affect the axial alignment between the tip of the needle and the opening area of the cannula.

In order to seal the needle in the opening of the cannula when the two elements are interconnected, the inner diameter of the cannula opening in the first element may be adapted in size to the outer diameter of the needle so that the needle is tightly and sealingly received in the cannula. This however would require highest precision in the manufacture of the first and also of the second elements since such tightly fitting engagement could be achieved only if the axis of the tubular cannula would be precisely aligned with the needle. It is therefore considered to be advantage us for achieving a sealing connection between the cannula and the needle if the cannula opening is covered by a closure element which is pierced during insertion of the needle into the opening area of the cannula that is when the second element is inserted into the insertion opening of the first element, that is when the two elements are properly positioned relative to each other and interlocked.

In order to ensure that, upon disconnection of the two elements and removal of the second element from the first element from the insertion opening, the exposed opening of the cannula is not contaminated, the closure element consists preferably of an elastomer or plastomer material. Such a material can easily be pierced by the needle and, upon removal of the needle, the passage pierced into the closure element is automatically closed because of the elastic or plastic properties of the material of which the closure element consists.

The essential elements of the infusion apparatus may be made of plastic. Any plastic material may be used which is neutral that is which is compatible with human or animal tissue. Preferably, the plastic material can be injection molded so that the injection apparatus can be manufactured by injection molding machines. A suitable plastic material is for example polycarbonate.

Since the locking elements are elastically deformed in their unlocking positions, the must be made of an elastically deformable material, preferably of polyacetate, which is a strong material with good elastic deformation characteristics.

In principle the cannula can be mounted in, that is, firmly connected with, the first element during the injection molding of the first element. It has been found to be advantageous to surround the cannula at its end in the first element with a sleeve element by way of which the cannula is received in a recess formed in one end of the insertion opening for the second element. In this way, the first element can be manufactured independently of the cannula. The cannula can then be mounted together with the sleeve element into the recess of the first element for connections with the first element. This arrangement is also advantageous because it facilitates an exchange, and also cleaning, of the cannula.

In order to omit the need for further mounting means for the cannula in the first element, it is advantageous if the opening in the first element forms a suitable reception, preferably a compression mount for the sleeve element.

It is further advantageous to arrange the closure element, through which the needle extends when the second element is inserted into the first element and which forms a dust and micro-organism barrier, within the sleeve element. In this way, the closure element is replaced with each exchange of the cannula. Finally, a connecting element may be disposed in front of the sleeve element by way of which the cannula is connected to the sleeve element. The connecting element may be disposed in the sleeve element in addition to the closure element and the cannula is also supported in the sleeve element by way of a connecting element.

In order to facilitate the insertion of the cannula into the body, the second element is provided in a second embodiment of the invention with a needle of such length that its tip projects from the cannula. After the cannula has been inserted into the body with the needle disposed in the cannula, the second element with the long needle is removed and another second element with a hollow needle as first described is inserted and locked in position in the first element for the administration of a medicine.

The infusion apparatus can be sterilized in a disassembled state or in an assembled state. Sterilization can be achieved for example by ionizing irradiation, for example, by β irradiation. However, it is also possible to sterilize the apparatus by means of an oxidizing gas such as ethylene gas. In order to ensure that also the interior of the first element is contacted by the oxidizing gas when the two elements are joined, the long needle may be hollow like an infusion needle and provided with an opening leading to the area adjacent the cannula opening in the first element when the first and second elements are joined. In this way, gas can be conducted from the needle tip to the hollow space within the first element and sterilize that area and then again be discharge through the annular space between the needle and the cannula.

Below, the invention will be described in greater detail on the basis of the accompanying drawings.

DESCRIPTION OF EMBODIMENT

Figure 1:
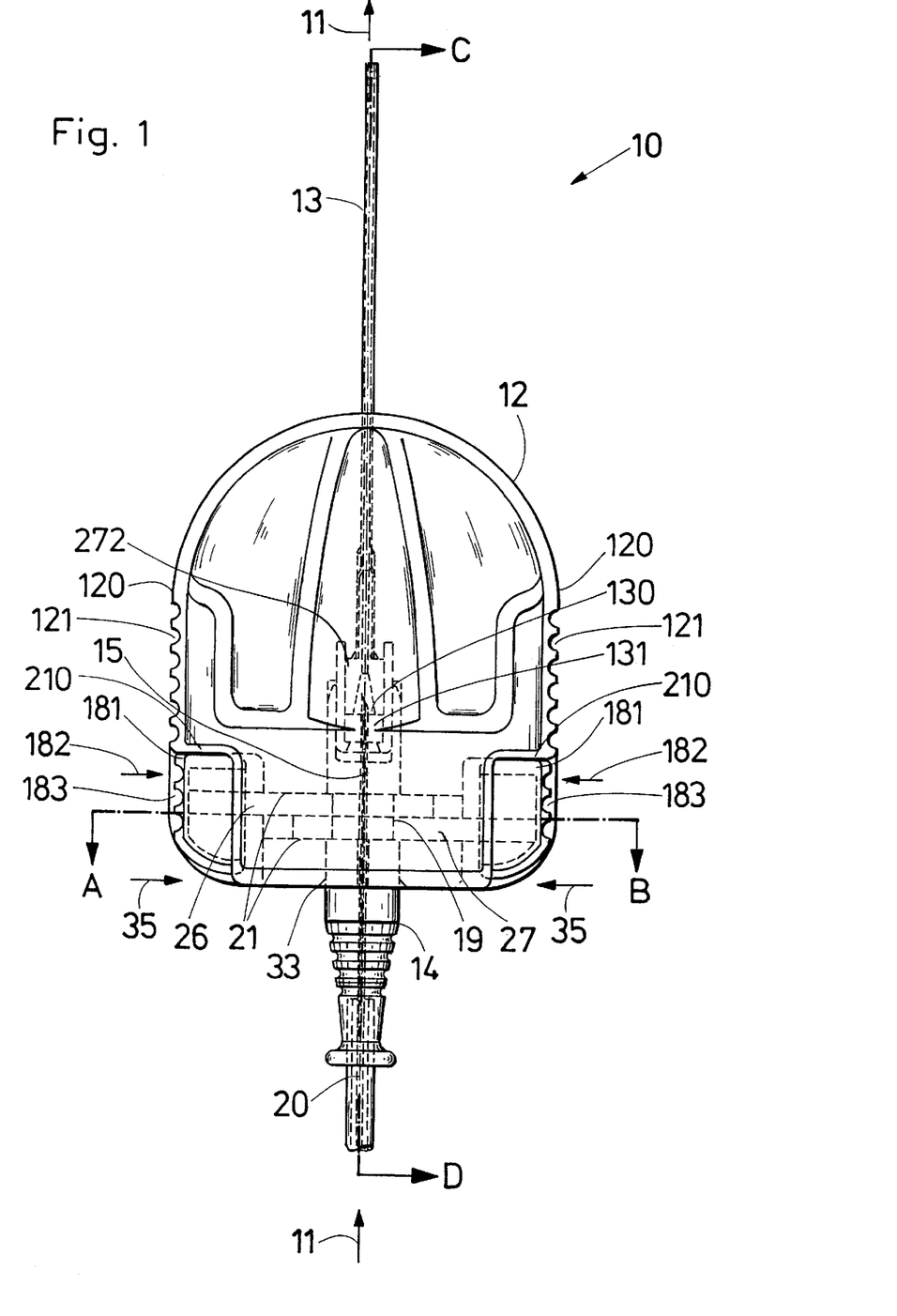
FIG. 1 is a top view of the infusion apparatus according to the invention including first and second elements shown interlocked with each other.

First, reference is made to FIG. 1 in which the whole infusion apparatus 10 is shown in a plain view. The infusion apparatus 10 comprises at least a first element 12, which includes a cannula 13 for insertion into the body of a patient (human, animal—not shown), and a second element 14. The second element 14 includes a needle 15, which is arranged essentially along the longitudinal axis 20 of the second element 14. The needle 15 is hollow that is it is in the form of an injection syringe needle. The needle 15 is connected in the second element 14 to a hose 17 for supplying a medicine, which is indicated in FIG. 1 by the arrow 11. When the first and second elements 12, 14 are interlocked as it is shown in FIG. 1, the medicine 11 can be conducted from the hose 17 through the needle 15 to the cannula 13 and, when the cannula 13 is inserted into the body of a human or an animal, into the tissue of the body. In order to ensure proper seating of the second element 14 in the first element 12 when the two elements are interconnected a locking structure is provided in the form of a locking means 22 (see FIG. 2).

Figure 2:
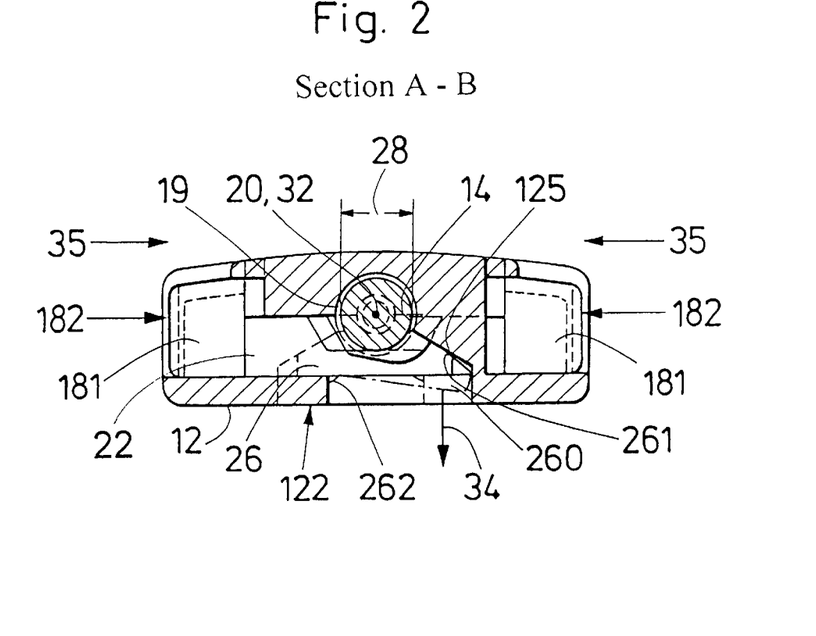
FIG. 2 is a cross-sectional view taken along line A–B of FIG. 1.
Figure 9:
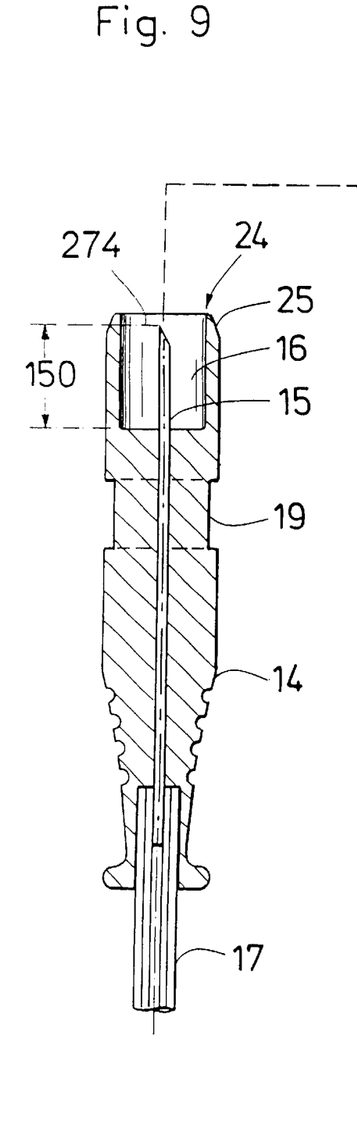
FIG. 9 is a cross-sectional view of the second element.

The locking structure comprises in addition to the locking member 22 a groove 19 formed in the second element 14, which has an essentially circular cross-section (see particularly FIGS. 2 and 9, indicated also in FIG. 1). The groove 19 extends essentially circularly around the second element 14. The groove 19 is disposed in the insertion area 23 (see FIGS. 6 and 7) of the second element 14 into the first element 12 that is in the section of the second element 14 which is received in the insertion opening 33 of the first element 12 when the first and second elements are interconnected.

The part of the locking structure which is disposed in the first element 12, that is, the locking means 22 is guided by a guide structure 21 which is formed so as to extend essentially normal to the axis 32 of the insertion opening 33. The guide structure 21 may simply be a slot-like recess (see FIG. 1) in which the locking means 22 can be moved back and forth (see FIGS. 1 and 2).

Reference is also made to FIGS. 4a and 4b and FIGS. 5a and 5b, which show the locking member 22 which forms the part of the locking structure disposed in the first element 12. The locking means 22 comprises two separate locking members 26, 27. The locking member members 26, 27 are essentially identical; only the actuating structure 181 which is connected to the locking member members 26, 27 or formed integrally therewith includes in the embodiment as presented in FIG. 1 a left side version (locking member members 26) and a right side version (locking member 27). The locking members 26, 27 include circular areas 263, 273. The radii 28 of these circular areas 263, 273 are the same as those of the groove 19 of the second element 14. The circular areas 263, 273 are shown here as quarter circle segments. The locking members 26, 27 include inclined ramp areas 261, 271 with lower heights at the free ends 260, 270.

Figure 6:
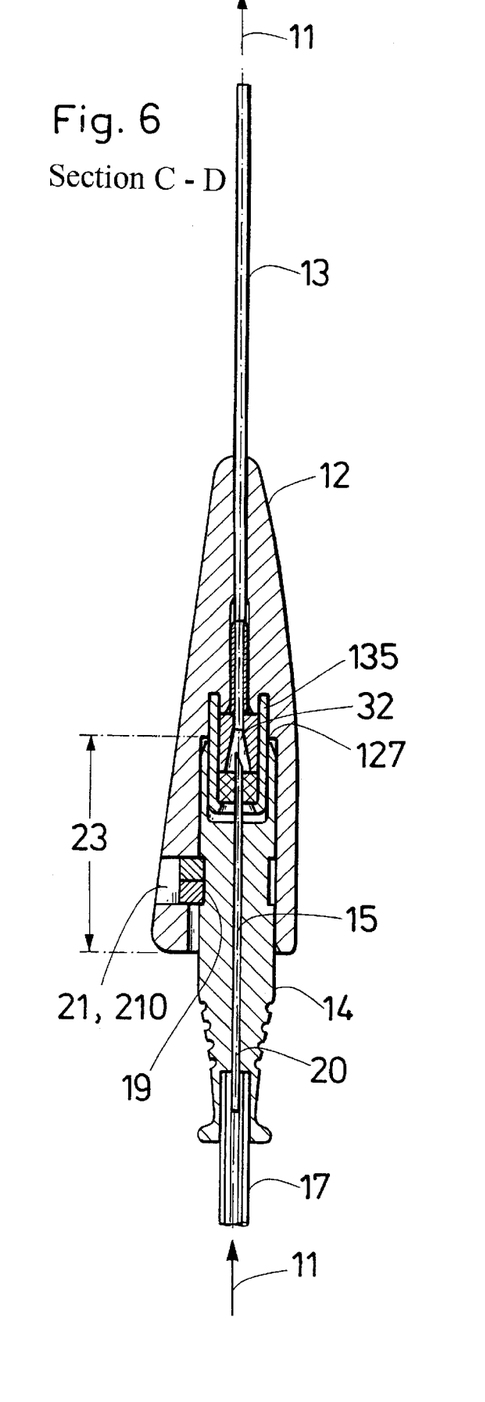
FIG. 6 is a cross-sectional view of the infusion apparatus of FIG. 1 taken along line C–D.
Figure 7:
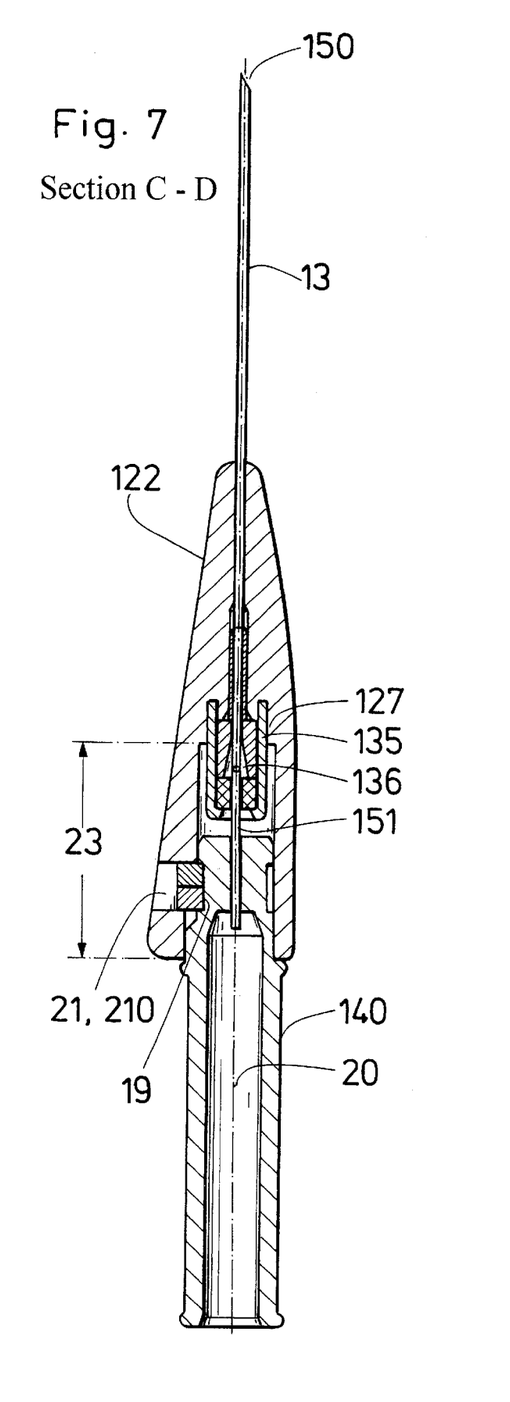
FIG. 7 is a side cross-sectional view of FIG. 1 also taken along line C–D wherein however the first element is connected to a second element which is modified to include a long needle extending all the way through the cannula of the first element.

The first elements 12 also includes inclined areas 125, 126 disposed in the guide structure 21 which is in the form of a guide slot 210 (see FIGS. 1, 6, 7).

If the actuating structures 181 of the two locking members 26, 27 are moved toward each other as indicated by the arrows 35 (see FIG. 2) to disengage the two elements 12, 14 from each other the inclined locking member areas 261, 271 of the locking members 26, 27 move onto the inclined areas 125, 126 of the guide structure 21 of the first element. As the inclined areas 261, 271 ride upon the inclined areas 125, 126, the locking member 26, 27 are elastically deflected in the direction of the arrow 34 as it is indicated in FIG. 2 for the locking member 26 by a dashed line. The same applies to the locking member 27, which is not shown in FIG. 2. Upon further movement of the locking members 26, 27 in the direction of the arrows 35, the locking members 26, 27 are disengaged from the groove 19 of the second element 14 so that the second element 14 is released and can be pulled out of the first element 12.

The locking members 26, 27 are guided in the guide structure 21, 210 parallel to each other and are movable in the guide structure back and forth in the direction of the arrow 35. In the direction of the arrows 35, the locking members 26, 27 are received by finger pressure. Movement in the direction opposite to the arrows 35 occurs as a result of the elastic return force of the locking members 26, 27 automatically when the finger pressure is released. As a result, the locking members 26, 27 are biased into a locking position by the elastic deformation forces. A material providing for good elastic deformation characteristics and a long operating life is for example polyacetate (POM) which is the preferred material for the manufacture of the locking members 26, 27.

Figure 3:
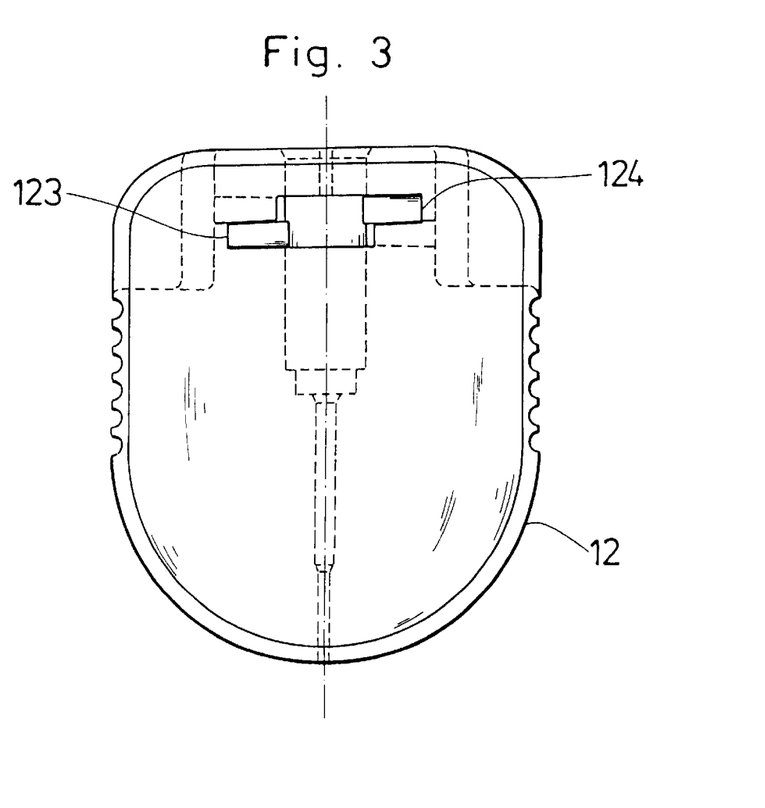
FIG. 3 is a bottom view of the first element.
Figure 4:
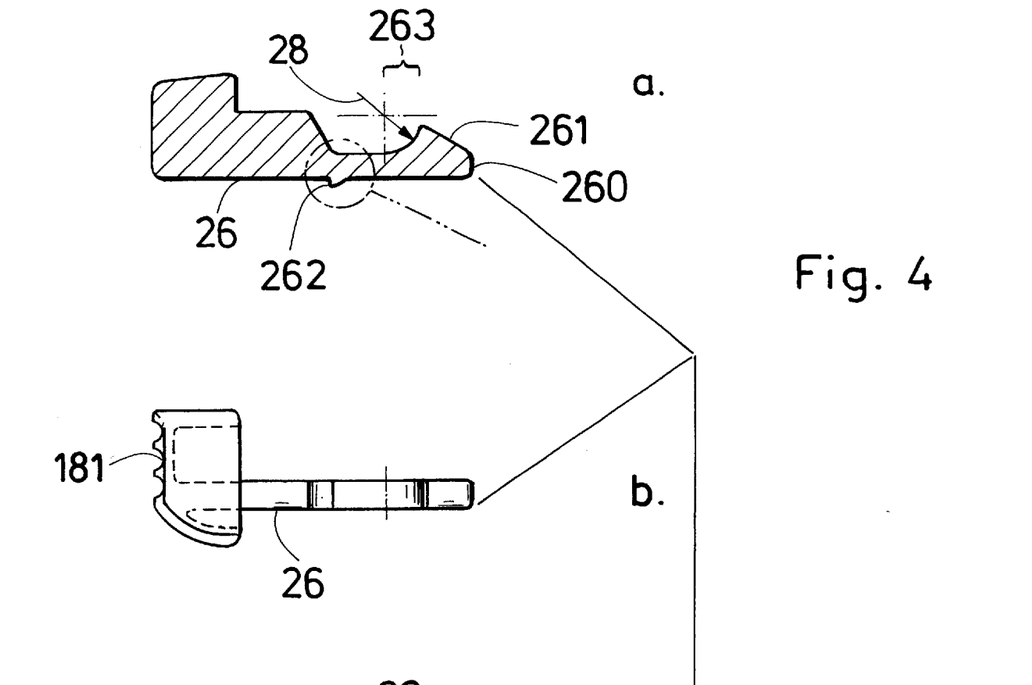
FIG. 4a is a cross-sectional view of the left locking member.
FIG. 4b is a plane view of the left locking member.
Figure 5:
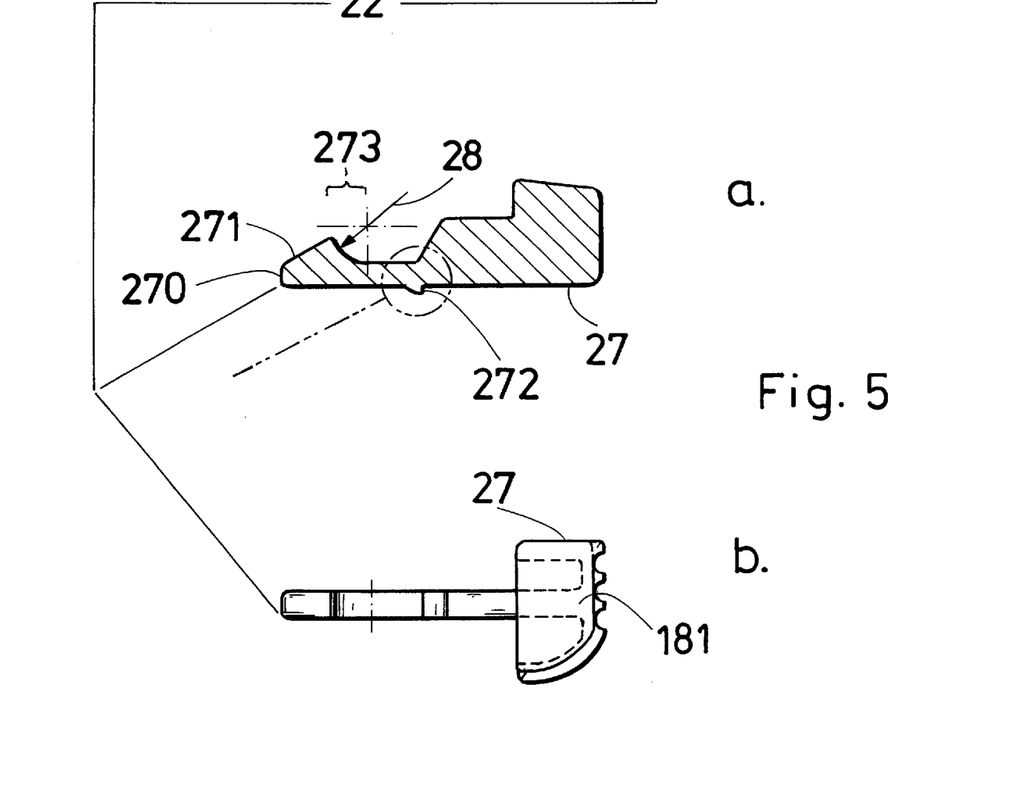
FIG. 5a is a cross-sectional side view of the right locking member.
FIG. 5b is a plain view of the right side-locking member.

The locking members 26, 27 each include an engagement projection 262, 272 (see FIGS. 4a, 5a). The engagement projections 262, 272 abut the edges 123, 124 of the guide structure 21 formed in the first element 12 (see FIG. 3). The engagement projections 262, 27 form, together with the engagement edges 123, 124, an engagement structure, whereby the locking member members 26, 27 are held in position when they are inserted into the guide structure 21, 210 upon assembly of the first element 12. In addition, the engagement projections 262, 272 form a movement limit for the sliding movement of the locking members 26, 27 opposite to the direction of the arrows 35 (see FIG. 2).

The insertion of the second element 14 into the insertion opening 33 of the first element 12 up to a safely locked engagement position in which the needle 15 is received in the cannula 13 is possible in two ways.

Either the second element 14 is simply inserted into the insertion opening 33 until its free end 24 abuts the locking members 26, 27 (see FIG. 2). The free end 24 is conical so that it has a circumferentially extending wedge-like front end. The inclination 25 is so selected that, upon further insertion of the second element into the insertion opening 33, the locking members 26, 27 are engaged at their circular areas 263, 273 and moved in the direction of the arrows 34. When the second element 14 is fully inserted into the insertion opening 33 of the first element 12, the locking members 26, 27 are in alignment with the groove 19. The locking members 26, 27 snap into the groove 19 and firmly lock the second element inserted in the first element.

With the second way of interconnecting the first and second elements, the second element is first inserted into the insertion opening 33 as described above until the second member comes into contact with the locking members 26, 27. Then the locking members 26, 27 are moved in the direction of the arrows 35 by pressing them together with two fingers (FIG. 2) whereupon the second element 14 can be moved into the insertion opening 33 up to the end position. Upon release of the locking members 26, 27, the locking members move back and enter the groove 19 under the return force generated by their resilient deformation for locking the member 14 in its final position within the insertion opening 33 of the first member 12. This locked end position is shown for example in FIG. 2.

The locking members 26, 27 may project slightly from the body of the first element 12 (see FIG. 1). At the free end 180 of each locking member 26, 27, there is an actuating structure 181 formed as a widened area of the locking members 26, 27, which actuating structure may also be guided by a guide structure 210. The actuating structure 181 includes an outer handling area which includes a grasping structure 183 to facilitate actuation thereof. The grasping structure 183 may comprise grooves or it may be provided with a slip-resistant element.

Also, the first element 12 (see FIG. 1) may be provided at the sides 120 thereof with a grasping structure 121 which facilitates holding and which may be formed like the grasping structure described earlier.

The sides 122 of the first element 12 (see FIG. 2), which will be disposed on the skin of a patient is essentially planar, but it may also be formed ergonomically corresponding to the shape of the body area of the patient where the infusion apparatus is disposed so that the patient is as little as possible inconvenienced by the infusion apparatus 10.

Figure 10:
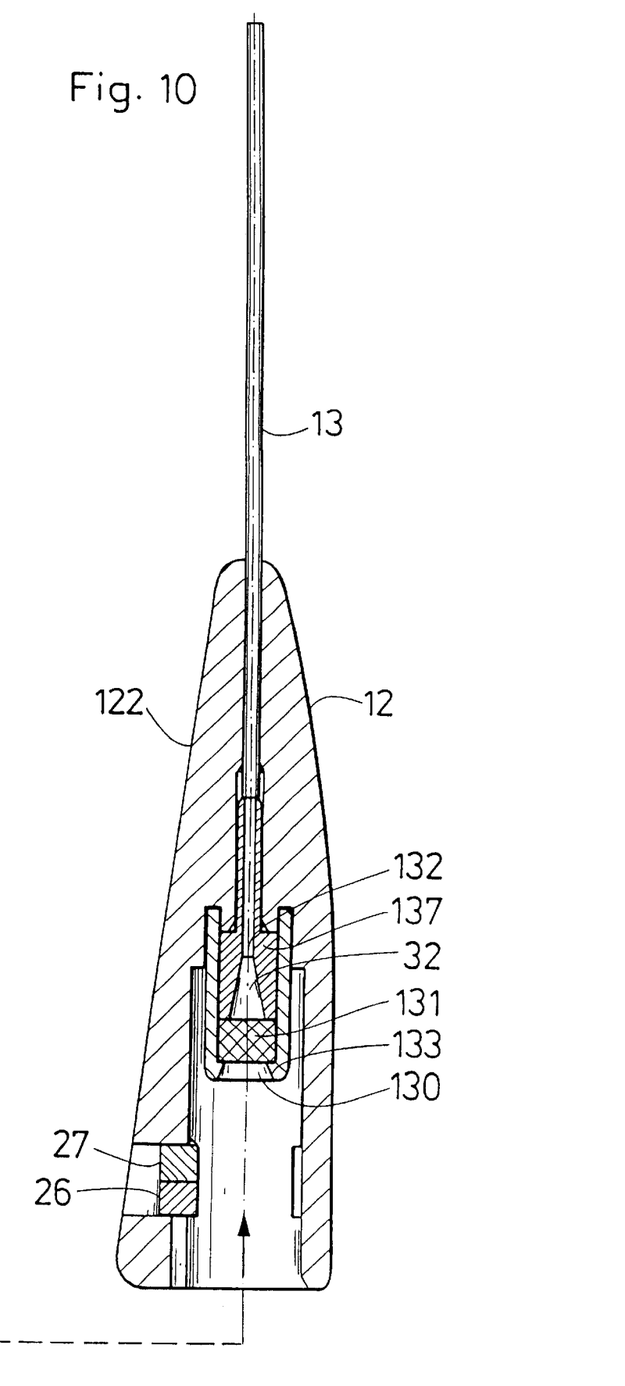
FIG. 10 is a cross-sectional view of the first element into which the first element of FIG. 9 is to be inserted as indicated by the dashed line extending between FIG. 9 and FIG. 10.

The second element 14 includes at its free end 24 an axial recess 274 into which the tip 150 of the needle 15 extends. The tip 150 extending into the recess 274 is so dimensioned that the tip 150 of the needle 15 does not project beyond the free end 24 (see FIG. 9). From FIG. 10, it can be seen that the opening 130 of the cannula 13 which faces the free end 24 of the second element 14, proyects into the insertion opening 33 in such a way that, when the first and the second elements 12, 14 are interconnected, the needle 15 can enter a closure element 131 which covers the widened opening of the cannula 13. The tip of the needle 15 is then disposed in the widened opening of the cannula 13 (see FIG. 6). The closure element 131 which is disposed adjacent the opening 130 of the guide means 133 may consist of an elastomer and/or polymer material for example of rubber or another mat rial suitable for use with humans or, respectively, animals.

Figure 8:
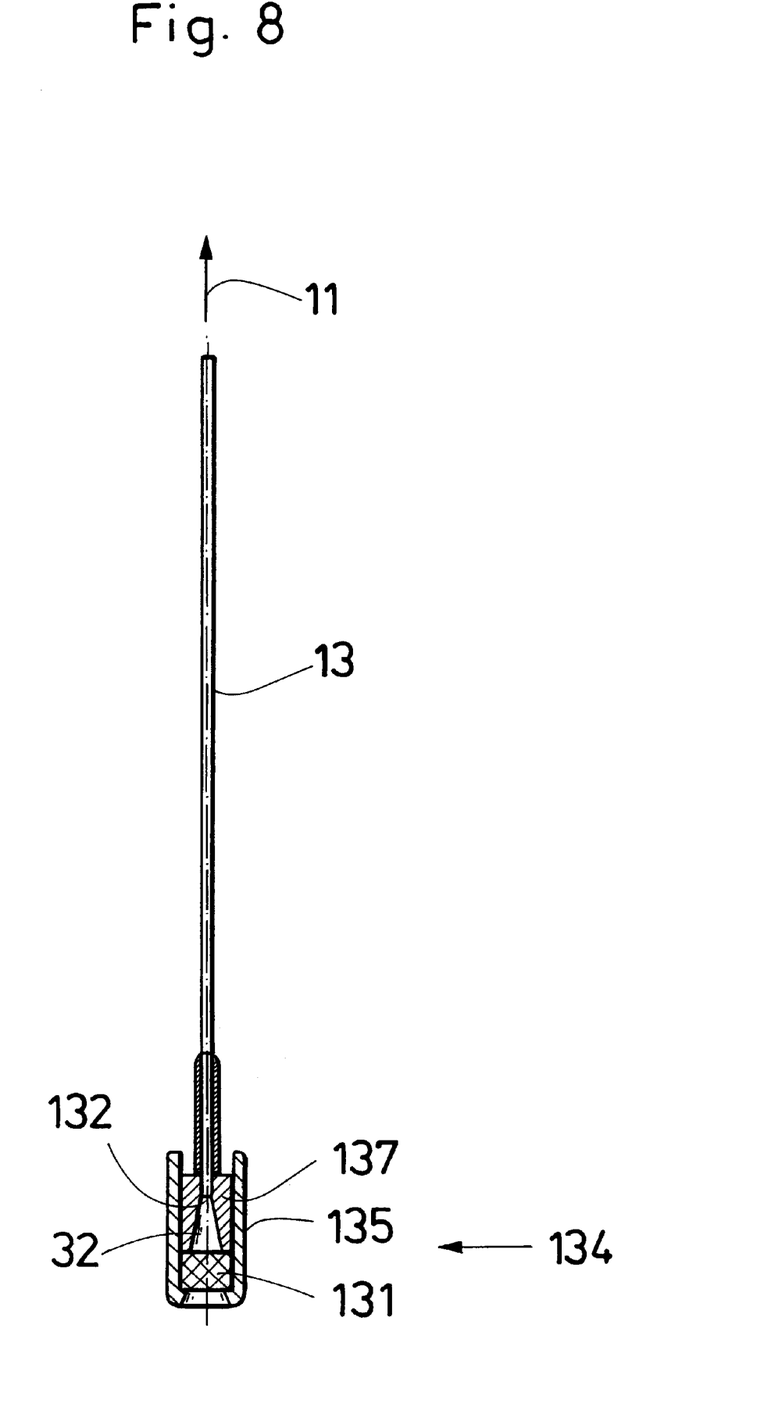
FIG. 8 shows the cannula with a sleeve element including a closure element all shown in cross-section.

The cannula 13 is surrounded, at its end 134 disposed in the first element 12 by a sleeve element 135 (see FIG. 8), in which the closure element 131 is received. Toward the medicine discharge end of the cannula, that is ahead of the closure element 131, a connecting element 137 is disposed in the sleeve element 135 by way of which the cannula 13 is joined to the sleeve element 135. The cannula 13 as well as the sleeve element 135 and the closure element 131 disposed therein and also the connecting element 137 form a mounting unit which can be inserted into the opening 127 formed in the first element 12. The opening 127 is sized so as to tightly engage the sleeve element 135 and retain it without the need for mounting means or other means for holding the sleeve element 135 safely in position in the sleeve element 12.

The axis 32 of the cannula 13 is preferably arranged at a slight angle of for example 3° relative to the essentially planar underside 122 of the first element 12 (FIG. 2) so that the cannula 13 is slightly inclined relative to the support surface (underside 122) of the first element 12.

Finally, reference is made to FIG. 7 in which an embodiment of the infusion apparatus is shown in a cross-sectional side view. The second element 140 shown in this embodiment is different from the second element 14 shown in the other figures in that the needle 151 is substantially longer than the needle 15. The second element 140 as shown in FIG. 7 is not connected to a hose 17 for the admission of the medicine 11; rather the needle 151 is mounted in a suitable manner in the front end of the second element 140 that is in the area where the second element 140 is connected to the first element 12 in the same way as described earlier for the interconnection of the elements 12 and 14. However, the needle 151 is so long that it fully extends through the cannula 13 and its tip 150 slightly projects from the cannula 13 when the second element 140 is fully inserted into, and locked to, the first element 12 (see FIG. 7).

When the infusion apparatus 10 is used for the first time, the configuration according to FIG. 7 is employed. The needle 151 can be easily inserted, in a well known manner, into the body of the patient to be treated. Together with the needle 151 also the cannula 13 can easily be inserted into the body.

When being inserted to the predetermined depth the second element 141 is pulled out of the first element 12 and, in place of the second element 140, the second element 14 is installed in such a way as it is shown in FIG. 6. The hollow needle 15 penetrates the closure element 31 so that the medicine can be supplied from the hose 17 to the cannula 13 and from there into the body of the patient to be treated. When, at the end of the treatment, the second element 14 is removed while the first element with the cannula 13 remains attached to the body, the closure element 131 closes and seals out any contamination upon removal of the second element 14.

The insertion needle 151 used in connection with the second element 140 may be solid, but it may also be hollow like an injection needle. If the long insertion needle 151 is hollow, that is, tubular, it is provided with an opening 136 (see FIG. 7). The opening 136 is so arranged that, with the first element 12 and the second element 140 interconnected, the opening is disposed in the area of the opening of the cannula 13 that is in the widening space in the connecting element 137, which is disposed in the sleeve element 135. Such hollow insertion needle 151 with an opening 136 is then provided when the infusion apparatus 10 is not sterilized by ionizing irradiation, for example, β-irradiation, but by possibly highly oxidizing gas. In that case, the gas can flow from the tip area 150 of the insertion needle 151 through the insertion needle 151 to the cannula opening 132 in the first element 12 and from there, by way of the opening 136 into the trough-like widening interior of the connecting element 137. From there, the oxidizing gas can flow through the annular space between the insertion needle 151 and the cannula 13 to the discharge end of the cannula 13 and, if desired, back into the flow circuit of the sterilizing gas.

What is claimed is:

1. An infusion apparatus for supplying a medicine into the body of a human or an animal, comprising a first element including a cannula for insertion into said body and a second element including a hollow injection-type needle, and a hose connected to said hollow needle, for supplying said medicine to said hollow needle, said second element being insertable in said first element in such a way that said medicine can be supplied from said hose through said needle to said cannula, a locking structure for locking said second element to said first element when said first and second elements are joined, said locking structure including a circular groove formed in said second element in a portion thereof extending around said needle, at least one locking member slidably supported in said first element so as to be movable back and forth in a plane normal to an axis of said second element when disposed in said first element and in alignment with the groove formed therein, said locking member having one end position in which a portion thereof is disposed in said groove for interlocking said first and second elements and another position in which said first and second elements are unlocked permitting the removal of said second member from said first member.

2. An infusion apparatus according to claim 1, wherein said second element has an essentially circular cross-section with said needle extending essentially through the center of said circular cross section.

3. An infusion apparatus according to claim 1, wherein the end of said second element, which is inserted into said first element, is chamfered so as to facilitate insertion of said second element into said first element.

4. An infusion apparatus according to claim 3, wherein said second element is provided at its free end with an axially extending recess and said needle is disposed in said recess such that its tip does not extend beyond the walls defining said recess.

5. An infusion apparatus according to claim 4, wherein said cannula of said first element extends into a sleeve element with an opening and said sleeve element extends into said recess of said second element when said second element is inserted into said first element.

6. An infusion apparatus according to claim 5, wherein the open area of a connecting element is closed by a closure element consisting of one of an elastomer and plastomer material.

7. An infusion apparatus according to claim 5, wherein said sleeve element is press-fitted into said first element and said cannula extends into said sleeve element which is disposed in an insertion opening formed in said first element for receiving said second element.

8. An infusion apparatus according to claim 7, wherein said sleeve element includes a connecting element, which is disposed between a closure element and said cannula and into which said cannula extends for connection with said sleeve element.

9. An infusion apparatus according to claim 1, wherein said locking structure includes two locking members which are supported in said first member in parallel relationship so as to be movable back and forth in opposition to each other.

10. An infusion apparatus according to claim 9, wherein each locking member includes a partial circular area with a radius corresponding to the radius of said groove of said second element for firmly engaging said second element when said locking members are disposed in said groove.

11. An infusion apparatus according to claim 9, wherein said locking members are slideably supported in guide slots and include ramp areas, and said guide slots include inclined areas on which said locking members ride up when moved toward each other, whereby they are spread a part elastically and lifted out of said groove of said second element for unlocking said second element from said first element.

12. An infusion apparatus according to claim 11, wherein said first element has an insertion opening for receiving said second element and said guide slots are disposed in a plane extending essentially normal to the axis of said insertion opening along which axis said second element is inserted into said first element.

13. An infusion apparatus according to claim 9, wherein said locking members each include an engagement projection and said guide structure include edges for engaging said projections when said locking members are in a locking position for retaining said locking members in said locking position.

14. An infusion apparatus according to claim 13, wherein said locking members have opposite outer ends, which are provided with grasping structures.

15. An infusion apparatus according to claim 14, wherein also said outer ends with said grasping structures are slideably guided in said first element.

16. An infusion apparatus according to claim 1, wherein at least one side of said first element has a shape providing for a smooth area.

17. An infusion apparatus according to claim 1, wherein at least said first and second elements and said locking members consist of a plastic material permitting their manufacture by injection molding.

18. An infusion apparatus according to claim 17, wherein said locking members consist of polyacetate (POM).

19. An infusion apparatus according to claim 1, wherein a second element including an insertion needle of such length is provided that the insertion needle extends through the cannula when said second element is joined to said first element, said insertion needle having a tip projecting from said cannula.

20. An infusion apparatus according to claim 19, wherein said insertion needle is a hollow infusion type needle and includes a side opening disposed in said connecting element when said first and second elements are joined for providing communication between the interior of said insertion needle with the annular space between said insertion needle and said cannula.

* * * * *